US006417391B2

(12) United States Patent
Bauer

(10) Patent No.: US 6,417,391 B2
(45) Date of Patent: *Jul. 9, 2002

(54) PROCESS FOR THE PREPARATION OF 2-METHYL-1,3-DICARBOXYLATES

(75) Inventor: Frank Bauer, Bonn (DE)

(73) Assignee: Degussa AG, Duesseldorf (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/415,062

(22) Filed: Oct. 12, 1999

(30) Foreign Application Priority Data

Oct. 12, 1998 (DE) .......................... 198 46 903

(51) Int. Cl.[7] .............................................. C07C 67/30
(52) U.S. Cl. .................. 560/203; 560/179; 560/180
(58) Field of Search ................ 560/179, 203, 560/180

(56) References Cited

U.S. PATENT DOCUMENTS 4,138,580 A * 2/1979 Umemura et al. ............ 560/81
4,251,447 A * 2/1981 Perrin ......................... 549/231
4,256,908 A * 3/1981 Nishimura et al. .......... 560/204
4,567,004 A * 1/1986 Umemura et al. ........... 558/372
4,894,471 A * 1/1990 Angeletti et al. ............ 558/378
5,233,078 A * 8/1993 Schuster et al. ............. 560/204

OTHER PUBLICATIONS

European Search Report Dated Jan. 12, 2000.

* cited by examiner

*Primary Examiner*—Paul J. Killos
*Assistant Examiner*—Taylor V. Oh
(74) *Attorney, Agent, or Firm*—Oblon, Spivak, McClelland, Maier & Neustadt, P.C.

(57) ABSTRACT

A process for the preparation of a 2-methyl-1,3-dicarboxylate by reaction of a 1,3-dicarboxylate with formaldehyde and hydrogen, where, based on 1 mol of dicarboxylate, from 1.0 to 2.0 mol of formaldehyde are used, and either the reaction mixture or 2-hydroxymethyl-2-methyl-1,3-dicarboxylate isolated therefrom as by-product are subjected to thermolysis at temperatures of from 50° C. to 300° C.

15 Claims, No Drawings

PROCESS FOR THE PREPARATION OF 2-METHYL-1,3-DICARBOXYLATES

BACKGROUND OF THE INVENTION

1. Field of the Invention

The present invention relates to a process for the preparation of 2-methyl-1,3-dicarboxylates.

2. Discussion of the Background

2-Methyl-1,3-dicarboxylates of formula I

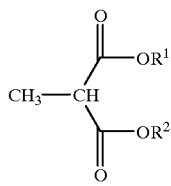

(I)

in which $R^1$ and $R^2$ independently of one another represent an alkyl, aralkyl, aryl or cycloalkyl group or are a common part of a hydrocarbon chain and, in particular, diethyl 2-methyl-1,3-dicarboxylate, are of great interest as organic intermediates in the preparation of pharmaceutically active ingredients or crop-protection compositions.

Methylation processes for the preparation of a compound of formula I described in the literature usually start from the corresponding unsubstituted 1,3-dicarboxylate of the formula

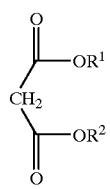

(II)

where $R^1$ and $R^2$ are defined as above. During methylation using usual alkylating agents, such as dimethyl sulfate or methyl bromide, mixtures of monomethylated products, dimethylated products and the unsubstituted starting materials are usually produced, which can only be removed by distillation with great difficulty.

A method which is better suited for obtaining pure monomethyl compounds of formula I involves reductive alkylation of the compounds of formula II by reaction with formaldehyde under hydrogenating conditions.

As described in DE-A-33 26 635, the disclosure of which is incorporated herein, very specific reaction conditions must be maintained in order to achieve relatively high conversions. Specifically, a process is described wherein a compound of formula II to be methylated is added to the mixture of the other reactants at an elevated temperature in the presence of both a Knoevenagel catalyst and a hydrogenation catalyst.

However, when a conventional amount of formaldehyde and solvent is used, quantitative conversion of the starting compounds of formula II is not achieved. The compounds of formula I prepared in this way can comprise from 0.5 to 2% of unreacted starting material, depending on the reaction conditions and the separation conditions chosen for the isolation of distillative product. In view of the fact that the compounds of formula I are used as intermediates for pharmaceuticals or crop-protection compositions, this result is completely unacceptable.

Accordingly, there is a need for a process for the preparation of compounds of formula I from the corresponding unsubstituted 1,3-dicarboxylates which produces the target products in high yields and with minimal content of unmethylated starting material.

SUMMARY OF THE INVENTION

It is an object of the invention to provide a process for preparing a 2-methyl-1,3-dicarboxylate in high yields with minimal production of by-products.

This and other objects of the invention have been achieved by reaction of a 1,3-dicarboxylate of formula II with formaldehyde and hydrogen, using, based on 1.0 mole of the dicarboxylate, from about 1.0 to about 2.0 mol of formaldehyde, and subjecting the reaction mixture or compounds isolated therefrom to thermolysis at a temperature of from about 50° C. to about 300° C.

DETAILED DESCRIPTION OF THE PREFERRED EMBODIMENTS

In the process according to the invention, a catalyst combination is used comprising a hydrogenation catalyst and a Knoevenagel catalyst. The Knoevenagel catalyst used in the reaction may be acidic or basic in character. Typical catalysts of this type are, for example, pyridine and/or aliphatic amines.

Hydrogenation catalysts which may be used include, for example, Raney nickel or precious metals such as palladium, platinum or rhodium in pure form or in combined compositions, preferably on support materials. Suitable supports include, for example, activated carbon or aluminum oxide. Preference is given to palladium on activated carbon.

Suitable starting materials for use in the process of the invention include compounds of formula II where $R^1$ and $R^2$ may be selected from optionally substituted straight chain or branched alkyl groups of about 1 to 12 carbon atoms, optionally substituted aralkyl groups containing up to about 12 carbon atoms (e.g., benzyl, phenethyl or the like), optionally substituted aryl groups containing up to about 12 carbon atoms (e.g., benzene, naphthalene), optionally substituted cycloalkyl groups of up to about 12 carbon atoms (e.g., cyclopentyl, cyclohexyl) and compounds where $R^1$ and $R^2$ together form a saturated or unsaturated hydrocarbon chain of up to about 12 carbon atoms (e.g., butylene, hexylene). Suitable optional substituents include halogen (e.g., chloro or bromo) lower alkyl, alkoxy, amino, etc.

With regard to the prior art process in DE-A-33 26 635, it has been observed that the yield of compounds of formula I drastically decreased with increased amounts of formaldehyde, based on the amount of the compound of formula II used, while the formation of 2-hydroxymethyl-2-methyl-1,3-dicarboxylates of formula III increased.

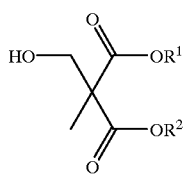

(III)

Thus, the by-product obtained in DE-A-33 26 635 during the reductive alkylation of diethyl malonate with formaldehyde and hydrogen is diethyl 2-hydroxymethyl-2-methylmalonate.

Further yield losses may result from ester condensation involving the hydroxymethyl group of the compound of formula III and may be observed in particular at temperatures greater than 100° C., which are desirable for the purpose of achieving high space-time yields. This also is a limitation with respect to conditions for distillative separation of compounds of general formula I from compounds of formula III formed as by-product. A further limitation may arise from the observation that during the distillation of mixtures of the compounds of formula I and compounds of formula III at industrially significant temperatures of greater than 50° C., decomposition reactions may cause formaldehyde to be liberated. In addition to contamination of the product, this can lead to deposits and, in the worst case, blockages in parts of the plant.

Surprisingly, it has been discovered that the amount of formaldehyde required to achieve a virtually quantitative conversion of the compounds of formula II without yield losses can be employed if the reaction mixture is subsequently subjected to thermolysis at from about 50° C. to about 300° C., preferably from about 100° C. to about 200° C., most preferably from about 130° C. to about 170° C.

It is possible to isolate the compounds of formula III formed under the preferred reaction conditions of reductive alkylation, and to subject them separately to thermolysis. In such cases, it has proven advantageous to employ a solvent which does not appreciably react with other components of the reaction mixture under the reaction conditions. Suitable solvents are: optionally halogenated aromatic or aliphatic hydrocarbons, alkanols (where $R^1=R^2$ ideally $R^1OH$, since this avoids the formation of mixed malonates), carboxylic acids, ethers, cyclic ethers and polyethers such as diethylene glycol diethyl ether. Ethanol or acetic acid is particularly suitable. Solvent mixtures are also possible. The solvent should, however, have adequate dissolving power for water since water formed during the reaction may lead to problems with the hydrogenation catalyst.

With the aim of minimizing the process steps, the process is advantageously carried out by using the same solvent or solvent mixture for the thermolysis step, as used for the reaction of the compounds of formula II with formaldehyde and hydrogen. In a particularly advantageous manner, it is possible to dispense with separation and separate thermolysis of the compounds of formula III. For this, the reaction mixture, which comprises the compounds of formulae I and III, the solvent, the hydrogenation catalyst and the Knoevenagel catalyst, may be subjected to thermolysis without further work-up or following simple removal of the usually solid hydrogenation catalyst.

During the thermolysis procedure, the formaldehyde/solvent mixture should be maintained in order to avoid p-formaldehyde formation which could obstruct the apparatus. The mixture could be used subsequently in a synthesis. For example, an ethanol/formaldehyde mixture could be employed in the synthesis of 2-methylmalonic acid diethyl ester and 2-hydroxymethyl-2-methylmalonic acid diethyl ester.

A prerequisite for successful recycling of the solvent or solvent mixture is always that the water formed during the reductive alkylation is at least partly removed prior to thermolysis or at least partial dewatering of the solvent or solvent mixture takes place prior to its reuse. Preferred solvents or solvent mixtures for the thermolysis step are those which can be easily freed of water.

The selectivity of the thermolysis reaction, i.e. the formation of 2-methyl-1,3-dicarboxylates at the expense of oligomers and polymers, and the reaction rate can be improved by adding suitable catalysts. Such catalysts include alkali metal salts such as potassium acetate and copper-containing catalysts such as copper salts, in particular copper(II) acetate, which are homogeneously dissolved in the reaction mixture. Fixed-bed catalysts can also be used. These are easier to handle and separate. Examples include aluminum oxides or catalysts such as copper-containing ones, fixed to a support material.

Catalyst amounts of from about 0.01 to about 50.0 g, preferably from about 0.05 g to about 5.0 g, per mole of compound of formula II usually suffice. Particular preference is given to amounts of about 0.1 to about 2.0 g, and most preferable from about 0.5 g to about 1.6 g of catalyst per mole of the compound of formula II.

When copper (II) acetate is used as the thermolysis catalyst, it is advantageous to add the catalyst in portions or continuously. If the catalyst has been added to the reaction mixture for the reductive alkylation, and, to increase the solubility of the catalyst, an acid such as acetic acid also has been added, the thermolysis yields decrease markedly if the reaction mixture is stored for a period of several hours.

Since the thermolysis reaction proceeds very quickly in the presence of catalysts and in particular at temperatures of greater than 80° C., the process according to the invention is advantageously carried out continuously. For this purpose, one can use, for example, a two-stage battery of stirred-tank reactors instead of a single reactor. However, the use of a falling-film, thin-layer or short-path evaporator as a thermolysis reactor has proven more favorable.

In addition to the advantage of a continuous and thus economical operation, one skilled in the art may also use mild reaction conditions, which effect rapid removal of 2-methyl-1,3-dicarboxylate from the reaction zone and thus minimize by-product formation. At the same time, the reverse reaction of compounds of formula I with liberated formaldehyde is suppressed.

In order to achieve rapid evaporation of the compounds of formula I, a vacuum is usually applied to the evaporator. The thermolysis is preferably carried out under a reduced pressure of from about 5 mbar to about 900 mbar, preferably from about 100 mbar to about 300 mbar.

Excellent yields and product purities are obtained when the compound of formula III or mixtures comprising the compound of formula III are added while distilling off the compound of formula I continuously into a hot thermolysis still.

It has been found that, particularly in the case of continuous thermolysis of a compound of formula III, very high and economically attractive throughputs can be achieved using the process of the invention when a low content of a compound of formula III is maintained in the thermolysates.

Because of the thermal sensitivity of the compound of formula III, difficulties may arise during distillative isolation of the product of formula I. It has been found that a thermolysate having a low content of a compound of formula III can be obtained at high throughputs if the thermolysis is carried out by subjecting the vapors which leave the thermolysis zone to fractionation, and returning the fraction rich in the compound of formula III, optionally after any desired catalyst and/or solvent has been added to the thermolysis zone. In the simplest case, the thermolysis is carried out using a thin-layer evaporator as a reactor, in which case a rectification unit consisting of, for example, bubble-cap trays or packing is present in the vapor line. The reflux of the rectification unit passes into the hot thermolysis zone. Alternatively, the reflux of the rectification unit can be pumped into the receiver of the thermolysis reactor where renewed mixing with the catalyst takes place.

Finally, any compound of formula III remaining in the thermolysate can be converted into thermally stable secondary products by derivatization with suitable derivatizing agents which convert the compound III into a temperature-stable secondary product which can be distilled. Suitable derivatizing agents include organic acids such as acetic acid, anhydrides thereof, higher carboxylic acids, acid chlorides and silylating agents such as trimethylsilyl chloride. A preferred derivatizing agent is acetic anhydride. As a result, even under industrial scale conditions, problem-free isolation of the compounds of formula I by fractional distillation can be achieved.

The present invention is illustrated in greater detail by the following examples, which are not intended to limit the scope of the claims unless otherwise specified.

EXAMPLE 1

Diethyl 2-methyl-1,3-dicarboxylate

A 1.5 l autoclave with lifter stirrer was charged, with stirring, with a mixture of 320.0 g of diethyl 1,3-dicarboxylate, 78.5 g of ethanol, 8.6 g of pyridine and 8.0 g of Pd/C (5%). The air in the autoclave was expelled by flushing three times with nitrogen and subsequently injecting 5 bar of hydrogen.

The mixture was then heated to 120° C. and the hydrogen pressure was adjusted to from 35 bar to 40 bar before 243.0 g of an ethanolic formaldehyde solution (66.0 g of p-HCHO in 177.0 g of ethanol; 10% excess) was metered into the autoclave over the course of 60 minutes using a piston pump. To transfer all of the formaldehyde to the autoclave, the metering system was then flushed with 39.3 g of ethanol.

The mixture was then left to react for a further 80 minutes at 120° C./35 bar and then cooled to room temperature and freed from catalyst by filtration. Product adhering to the catalyst was transferred to the filtrate by washing with 39.3 g of ethanol.

This filtrate was freed from low-boiling components at 60° C./10 mbar to leave 338.0 g of a clear colorless residue. The product ratio of diethyl 2-methyl-1,3-dicarboxylate to diethyl 2-hydroxymethyl-2-methyl-1,3-dicarboxylate, determined by gas chromatography, was about 7:1 based on FID area percentages after silylation. The content of unreacted diethyl 1,3-dicarboxylate in the residue was determined as 3.0 FID area percent after silylation.

EXAMPLE 2

Diethyl 2-methyl-1,3-dicarboxylate
Hydrogenation step:

A 5.0 liter autoclave with lifter stirrer was charged, with stirring, with a mixture of 1600.0 g of diethyl 1,3-dicarboxylate, 392.5 g of ethanol, 86.0 g of triethylamine and 40.0 g of Pd/C (5%). The air in the autoclave was expelled by flushing three times with nitrogen and subsequently injecting 5 bar of hydrogen.

The mixture was then heated to 120° C. and the hydrogen pressure was adjusted to from 35 bar to 40 bar before 1403.0 g of an ethanolic formaldehyde solution (400.8 g of p-HCHO in 1002.2 g of ethanol; 33% excess) was metered into the autoclave over the course of 60 minutes using a piston pump. To transfer all of the formaldehyde to the autoclave, the metering system was then flushed with 39.3 g of ethanol.

The mixture was then left to react for a further 80 minutes at 120° C./35 bar and then cooled to room temperature and freed from catalyst by filtration. Product adhering to the catalyst was transferred to the filtrate by washing with 39.3 g of ethanol. This gave 3559.6 g of a clear, almost colorless solution of diethyl 2-methyl-1,3-dicarboxylate and diethyl 2-hydroxymethyl-2-methyl-1,3-dicarboxylate in ethanol/triethylamine. The product ratio of diethyl 2-methyl-1,3-dicarboxylate to diethyl 2-hydroxymethyl-2-methyl-1,3-dicarboxylate, determined by gas chromatography, was about 3:1 based on FID area percentages after silylation.
Thermolysis step:

1423.8 g of the filtered hydrogenation product were admixed, with stirring, with 100.0 g of acetic acid (96% strength) and 8.0 g of copper(II) acetate hydrate and then stirred vigorously for 15 minutes at 45° C. in order to bring the catalyst completely into solution.

The resulting turquoise-colored solution was metered into a 250 ml thermolysis flask with attached splash guard and 30 cm packed column at a reduced pressure of about 90 mbar. The thermolysis flask, which contained a magnetic stirrer core for thoroughly mixing the bottom product which forms during the thermolysis and is of low viscosity at elevated temperature, was heated by means of an oil bath at 200° C.

The metering rate was controlled such that the internal temperature (gas phase and later also bottom product) was about 130° C. Under said conditions, thermolysis required about 5 hours.

The vapors produced at the head of the packed column were passed via an unheated vapor pipe into another packed column with a 30 cm stripping section and a 60 cm concentrating section. In this column, the low-boiling components (ethanol, water, HCHO) were separated from the diethyl 2-methyl-1,3-dicarboxylate, which was drawn off from the bottom of the column.

In this way, it was possible to obtain 78% of theory of diethyl 2-methyl-1,3-dicarboxylate, based on the amount of diethyl 1,3-dicarboxylate used, with a content of unsubstituted diethyl 1,3-dicarboxylate of <500 ppm.

EXAMPLE 3

Diethyl 2-methyl-1,3-dicarboxylate
Hydrogenation step:
The procedure was as described in Example 1.
Thermolysis step:

In each case 500.0 g or 423.8 g of the filtered hydrogenation product were admixed with stirring with a total of 40.0 g of acetic acid (96% strength) and a total of 6.5 g of copper(II) acetate hydrate and then stirred vigorously in each case for 5 minutes at 45° C. in order to bring the catalyst completely into solution.

The resulting turquoise-colored solution was metered continuously onto a thin-layer evaporator (evaporation surface area: 700 cm²) with attached 30 cm packed column, at a metering rate of about 1100 g/hour and at an evaporator jacket temperature of 220° C. and a reduced pressure of about 155 mbar. After the low-boiling components had been continuously removed by feeding the vapors into a column with stripping and concentrating sections, 80% of theory of diethyl 2-methyl-1,3-dicarboxylate, based on the amount of diethyl 1,3-dicarboxylate used, having a content of unsubstituted diethyl 1,3-dicarboxylate of <500 ppm was obtained.

EXAMPLE 4

Diethyl 2-methyl-1,3-dicarboxylate
Hydrogenation step:
The procedure was as described in Example 1.
Thermolysis step:
The procedure was as described in Example 2, but with recycling of the reflux of the column used for the separation of diethyl 2-hydroxymethyl-2-methyl-1,3-dicarboxylate and diethyl 2-methyl-1,3-dicarboxylate into the metering receiver of the evaporator. In this way, a yield of 85% of theory of diethyl 2-methyl-1,3-dicarboxylate, based on the amount of diethyl 1,3-dicarboxylate used, having a content of unsubstituted diethyl 1,3-dicarboxylate of <500 ppm was obtained.

EXAMPLE 5

Diethyl 2-methyl-1,3-dicarboxylate
Hydrogenation step:
The procedure was as described in Example 1.
Thermolysis step:
1423.8 g of the filtered hydrogenation product were freed from solvent by distillation, and admixed, with stirring, with 40.0 g of acetic acid (96% strength) and 8.0 g of copper (II) acetate hydrate. The resulting solution was stirred for 2 hours at 120° C. and then separated off from the catalyst by distillation.

In this way, a yield of diethyl 2-methyl-1,3-dicarboxylate of 76% of theory, based on the amount of diethyl 1,3-dicarboxylate used, having a content of unsubstituted diethyl 1,3-dicarboxylate of <500 ppm was obtained.

This application is based on German Priority Patent Application No. 19846903.9, filed Oct. 12, 1998, the entire contents of which are hereby incorporated by reference.

What is claimed is:
1. A process for the preparation of a 2-methyl-1,3-dicarboxylate of formula I

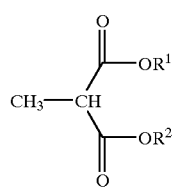

(I)

in which $R^1$ and $R^2$ independently of one another, represent a substituted or unsubstituted alkyl, aralkyl, aryl or cycloalkyl group having from 1 to about 12 carbon atoms or are a common part of a hydrocarbon chain, which comprises:

(1) reacting a 1,3-dicarboxylate of formula II

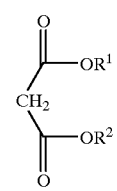

(II)

with hydrogen and about 1.0 to about 2.0 moles of formaldehyde per mol of said dicarboxylate of formula II, in the presence of a solvent, and a mixture of a hydrogenation catalyst and a Knoevenagel catalyst, wherein the improvement comprises (2) subjecting either the reaction mixture or a compound of formula III

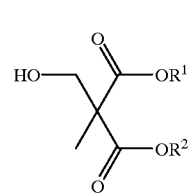

(III)

isolated therefrom, to thermolysis at a temperature of from about 50° C. to about 300° C. in an open system, wherein vapors which are produced during said thermolysis are removed.

2. The process as claimed in claim 1, wherein said thermolysis is carried out in the presence of at least one solvent which optionally, is identical to that used in step (1).

3. The process as claimed in claim 1, wherein the thermolysis is carried out in the presence of a homogeneously dissolved catalyst, in an amount of from about 0.01 g to about 50.0 g, per mole of the 1,3-dicarboxylate of formula II.

4. The process as claimed in claim 3, wherein the homogeneously dissolved catalyst is a copper compound.

5. The process as claimed in claim 1, wherein the thermolysis is carried out in the presence of a copper-containing catalyst fixed to a support material.

6. The process as claimed in claim 1, wherein the thermolysis is carried out under a reduced pressure of from about 5 mbar to about 900 mbar.

7. The process as claimed in claim 1, wherein the solution used in the thermolysis is fed to a reaction medium which is circulated over a fixed-bed catalyst and heated to thermolysis temperature.

8. The process as claimed in claim 1, wherein the solution used for the thermolysis is fed into a reaction medium which contains a homogeneously dissolved catalyst, heated to thermolysis temperature and circulated over a heat exchanger.

9. The process as claimed in claim 1, wherein the thermolysis is carried out continuously.

10. The process as claimed in claim 1, wherein the reaction mixture is subjected to thermolysis, optionally with removal of the hydrogenation catalyst.

11. The process as claimed in claim 1, wherein compound of formula III unreacted during the thermolysis is subjected to thermolysis, optionally with the addition of catalyst.

12. The process as claimed in claim 1, wherein any compound of formula III unreacted during thermolysis is converted into secondary products which optionally are removed by distillation.

13. The process according to claim 12, wherein said conversion involves reaction with acetic anhydride.

14. The process according to claim 1 wherein the thermolysis is conducted at a temperature of about 130° C. to about 170° C.

15. The process according to claim 3 wherein the amount of catalyst ranges from about 0.1 to about 2 g per mole of the 1,3-dicarboxylate of Formula II.

* * * * *